(12) United States Patent
Korytov et al.

(10) Patent No.: US 10,231,801 B2
(45) Date of Patent: *Mar. 19, 2019

(54) TRACKING TEETH MOVEMENT CORRECTION

(71) Applicant: Align Technology, Inc., San Jose, CA (US)

(72) Inventors: Viacheslav V. Korytov, Moscow (RU); Roman A. Roschin, Moscow (RU)

(73) Assignee: Align Technology, Inc., San Jose, CA (US)

( * ) Notice: Subject to any disclaimer, the term of this patent is extended or adjusted under 35 U.S.C. 154(b) by 324 days.

This patent is subject to a terminal disclaimer.

(21) Appl. No.: 15/056,617

(22) Filed: Feb. 29, 2016

(65) Prior Publication Data
US 2016/0175069 A1   Jun. 23, 2016

Related U.S. Application Data

(60) Continuation of application No. 13/893,661, filed on May 14, 2013, now Pat. No. 9,271,809, which is a division of application No. 13/017,913, filed on Jan. 31, 2011, now Pat. No. 8,439,673, which is a continuation of application No. 11/712,074, filed on Feb. 28, 2007, now Pat. No. 7,878,804.

(51) Int. Cl.
| | |
|---|---|
| *A61C 7/00* | (2006.01) |
| *G16H 50/50* | (2018.01) |
| *A61C 7/08* | (2006.01) |
| *A61B 6/14* | (2006.01) |
| *A61B 5/00* | (2006.01) |
| *G06F 19/00* | (2018.01) |

(52) U.S. Cl.
CPC ............ *A61C 7/002* (2013.01); *A61B 5/0088* (2013.01); *A61B 6/14* (2013.01); *A61C 7/00* (2013.01); *A61C 7/08* (2013.01); *G06F 19/00* (2013.01); *G16H 50/50* (2018.01)

(58) Field of Classification Search
CPC .. A61C 7/002; A61C 7/00; A61C 7/08; G16H 50/50; G06F 19/3437; A61B 5/0088; A61B 6/14
USPC ....................................................... 433/6, 24
See application file for complete search history.

(56) References Cited

U.S. PATENT DOCUMENTS

| | | |
|---|---|---|
| 5,975,893 A | 11/1999 | Chishti et al. |
| 6,457,972 B1 | 10/2002 | Chishti et al. |
| 6,488,499 B1 | 12/2002 | Miller |
| 6,512,994 B1 | 1/2003 | Sachdeva |
| 6,621,491 B1 | 9/2003 | Baumrind et al. |

(Continued)

*Primary Examiner* — Yogesh Patel
(74) *Attorney, Agent, or Firm* — Brooks, Cameron & Huebsch, PLLC

(57) ABSTRACT

Embodiments are provided for tracking teeth movement correction. One method embodiment includes using a set of positioning appliances shaped to move teeth through a number of successive stages of arrangements of an expected teeth arrangement model where each stage corresponds to a particular positioning appliance, mapping a current teeth position based upon positions of a number of physical markers attached to a number of physical teeth, comparing the positions of the number of physical markers with a corresponding number of virtual markers positioned on a number of virtual teeth of a stage in the expected teeth arrangement model, determining whether midcourse correction is needed.

19 Claims, 3 Drawing Sheets

(56) References Cited

U.S. PATENT DOCUMENTS

| | | | |
|---|---|---|---|
| 6,761,560 B2 | 7/2004 | Miller | |
| 6,947,038 B1 | 9/2005 | Anh et al. | |
| 7,063,532 B1 | 6/2006 | Jones et al. | |
| 7,077,647 B2 | 7/2006 | Choi et al. | |
| 7,125,248 B2 | 10/2006 | Phan et al. | |
| 7,134,874 B2 | 11/2006 | Chishti et al. | |
| 8,439,673 B2 | 5/2013 | Korytov et al. | |
| 2006/0099545 A1* | 5/2006 | Lai | A61C 7/00 433/6 |
| 2008/0206700 A1* | 8/2008 | Korytov | A61C 7/00 433/2 |
| 2008/0280247 A1 | 11/2008 | Sachdeva et al. | |

* cited by examiner

TRACKING TEETH MOVEMENT CORRECTION

RELATED APPLICATIONS

This application is a continuation of U.S. application Ser. No. 13/893,661, filed May 13, 2013, now U.S. Pat. No. 9,271,809, which is a divisional of U.S. patent application Ser. No. 13/017,913 filed Jan. 31, 2011, now U.S. Pat. No. 8,439,673, which is a continuation of U.S. patent application Ser. No. 11/712,074 filed on Feb. 28, 2007, now U.S. Pat. No. 7,878,804 the entire contents of which are hereby incorporated by reference.

BACKGROUND

The present disclosure is related generally to the field of orthodontics. More particularly, the present disclosure is related to a dental model system which can be manipulated to model a series of tooth configurations for a single patient throughout orthodontic treatment.

Many orthodontic treatments involve repositioning misaligned teeth and changing bite configurations for improved cosmetic appearance and dental function. Repositioning can be accomplished, for example, by applying controlled forces to one or more teeth over a period of time.

Some orthodontic processes use positioning appliances for realigning teeth. Such appliances may utilize a thin shell of material having resilient properties, referred to as an "aligner" that generally conforms to a patient's teeth but is slightly out of alignment with the initial tooth configuration.

Placement of such an appliance over the teeth provides controlled forces in specific locations to gradually move the teeth into a new configuration. Repetition of this process with successive appliances that provide progressive configurations eventually move the teeth through a series of intermediate arrangements to a final desired arrangement. An example of such a system is described in U.S. Pat. No. 5,975,893.

Such systems generally rely on designing and fabricating some, most, or all of the appliances, to be worn by the patient, at the outset of treatment. In some processes the design of the appliances relies on computer modeling of a series of successive tooth arrangements and the individual appliances are designed to be worn over the teeth and to reposition the teeth by using the appliances in a serial order, progressing from a first appliance, through each of the intermediate appliances, to the last appliance.

The set of appliances that is designed and fabricated at the outset of the treatment is typically planned to reposition the teeth to a final desired arrangement. In some cases, the treatment deviates from the planned process. Such deviations can arise from for example, poor patient compliance, or other factors.

The deviations will usually become apparent when the next appliance to be worn in the set of successive appliances does not fit as expected or upon a checkup by the orthodontist where the orthodontist notices that progress is not being made as planned. When a subsequent appliance has a poor fit, it indicates that the tooth arrangement has not progressed to the desired intermediate stage and that the teeth are not ready for the next appliance.

When such deviations occur, the response has usually been to restart the alignment process by creating new appliances based upon the current positioning of the teeth. In order to accomplish this, the location of the teeth has to be re-established and another set of appliances are then planned and fabricated to bring the teeth from the current intermediate arrangement to the desired final arrangement, which is usually the same, or close to the same, as the final arrangement that was the target of the original set of appliances.

Restarting the process, however, can be inefficient and wasteful. For example, in such instances, a number of additional appliances have to be fashioned in order to start the process again at a new (intermediate) starting point. Additionally, the remaining appliances from the original set will usually be discarded, since the treatment plan has been substantially redone, in many instances.

DETAILED DESCRIPTION

According to the present disclosure, systems and methods are provided for tracking teeth movement correction and/or determining a restart position within a number of stages of incrementally moving teeth using a plurality of discrete appliances, where each appliance successively moves one or more of the patient's teeth by relatively small amounts. The tooth movements are those normally associated with orthodontic treatment, including translation in the three orthogonal directions relative to a vertical centerline, rotation of the tooth centerline in two orthodontic directions ("root angulation" and "torque"), as well as rotation about the centerline.

Figure 1:
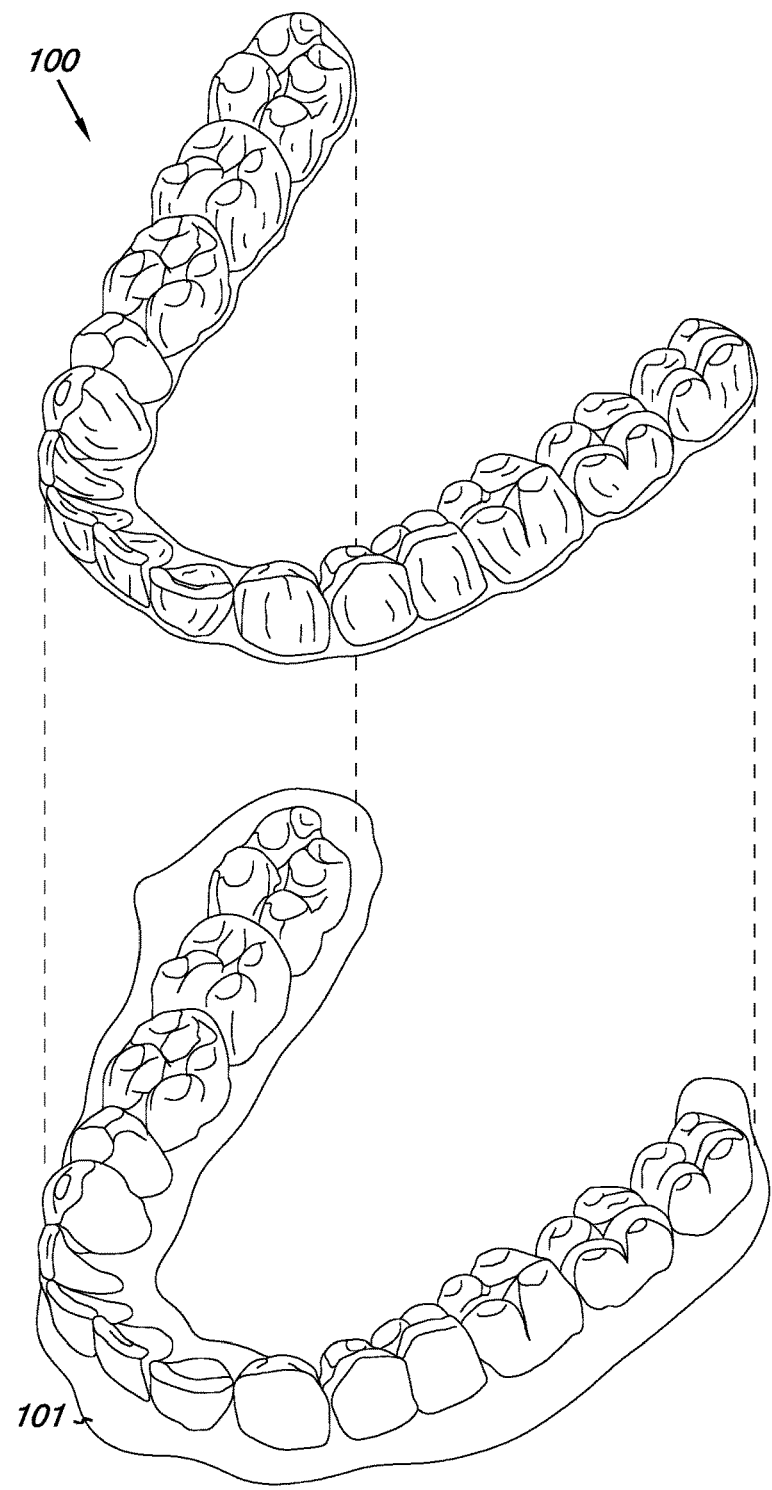
FIG. 1 illustrates a jaw of a subject together with an example of an incremental position adjustment appliance suitable for use with embodiments of the present disclosure.

Referring now to FIG. 1, systems according to the present disclosure include a plurality of incremental position adjustment appliances. The appliances are intended to affect incremental repositioning of individual teeth in the jaw as described generally above.

The methods of the present disclosure can employ any positioners, retainers, and/or other removable appliances for finishing and maintaining teeth positions in connection with orthodontic treatment. The systems for use with embodiments of the present disclosure provide a plurality of such appliances intended to be worn by a patient successively in order to achieve the gradual tooth repositioning as described herein.

An appliance 100 can, for example, be fabricated from a polymeric shell having a cavity shaped to receive and resiliently reposition teeth from one teeth arrangement to a successive teeth arrangement. The polymeric shell may be designed to fit over a number of, in many instances all teeth, present in the upper or lower jaw 101.

In some situations, certain individual or small sets of the teeth will be repositioned while others of the teeth will provide a base or anchor region for holding the repositioning appliance in place as it applies the resilient repositioning force against the tooth or teeth to be repositioned. In complex cases, however, many or most of the teeth will be repositioned at some point during the treatment.

In such cases, one or more of the teeth which are moved can also serve as a base or anchor region for holding the repositioning appliance. Additionally, the gums and/or the palette can serve as an anchor region, thus allowing all or nearly all of the teeth to be repositioned at the same time. In some cases, however, individual attachments (e.g., attachment 216 of the embodiment of FIG. 2) may be affixed on one or more of the teeth with corresponding receptacles or apertures in the appliance 100.

Figure 2:
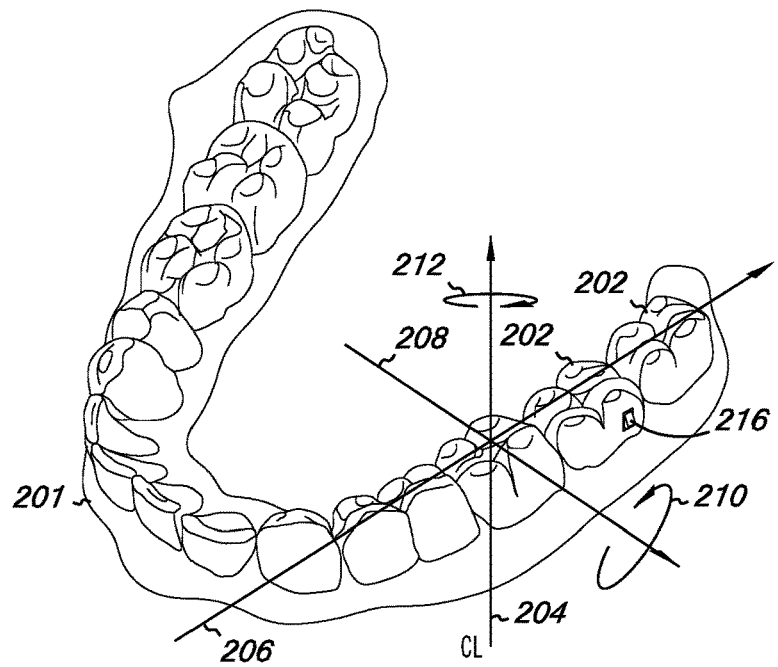
FIG. 2 illustrates a patient's jaw and provides a general indication of how teeth may be moved by the methods and apparatuses of the present disclosure.

Referring now to FIG. 2, a representative jaw 201 includes sixteen teeth 202. The embodiments of the present disclosure are intended to move one or more of these teeth from an initial tooth arrangement to a final tooth arrangement.

To understand how the teeth may be moved, an arbitrary centerline (CL) is drawn through one of the teeth 202. With reference to this centerline (CL), the teeth may be moved in the orthogonal directions represented by axes 204, 206, and 208 (where 204 is the centerline).

The centerline may be rotated about the axes 208 (root angulation) and 204 (torque) as indicated by arrows 210 and 212, respectively. In some embodiments, the tooth can be moved in the six degrees of freedom as they are understood by those of skill in the art. Of course, based upon the fact that a tooth is fixed in tissue, the freedom to move a tooth in any direction is not limitless.

In determining the current status of the teeth and how their position compares to one or more of the available appliances during the treatment process, in some embodiments, the current teeth position can be mapped based upon positions of a number of physical markers attached to a number of physical teeth. The physical markers can be any suitable marker type and can be permanently or temporarily fixed to one or more of the teeth to be analyzed.

Various examples of suitable physical markers are discussed below in more detail with respect to FIG. 3. In some embodiments, an attachment, or other dental component, can be used as a physical marker. For example, in FIG. 2, the attachment 216, or parts thereof (e.g., a corner, edge, etc), can be used a one or more physical markers. In embodiments, where the current teeth are mapped, the mapping process can be accomplished, for example, by taking an image of at least one of the number of physical markers. Any suitable image taking device can be utilized including two and three dimensional imaging devices. In such embodiments, this information can be analyzed by a computing device once the information is input into the computing device.

This input can be accomplished by any suitable digital input mechanism. Scanning the image or taking a digital image are such suitable mechanisms for inputting the information.

In various embodiments, the positions of the number of physical markers can be compared with a corresponding number of virtual markers positioned on a number of virtual teeth of a stage (i.e., visually illustrated as a virtual teeth model) in the expected teeth arrangement model. For example, if the markers are applied at the time that the expected teeth arrangement model is created and the information about those original positions is kept, then the current positions can be compared to the original positions or to later positioning within the arrangement model.

In instances where the markers were not added when the model was created, the markers can be applied to the teeth and then the information can be compared to a virtual teeth model. This process can be aided by creating virtual teeth markers to be used for comparison.

In such embodiments, if the virtual and physical markers are positioned in the same places on the one or more teeth being analyzed, then the difference in position can be more precisely accomplished, in some instances. For these virtual and/or physical markers, positional information can be used to identify the position of one or more teeth in the virtual model and/or the physical teeth arrangement and can be used to determine which appliance may be the best point to restart a treatment process.

As discussed above, an expected teeth model can also include information about the set of positioning appliances that have been fabricated for a particular patient and have been shaped to move teeth through a number of successive stages of arrangements of an expected teeth arrangement model where each stage corresponds to a particular positioning appliance can be used. In such embodiments, the information about the current teeth can be compared with the information about the positioning appliances to determine whether midcourse correction is needed. If it is determined that midcourse correction is needed, then a determination of which particular positioning appliance would be most suitable for restarting a treatment process can be made based upon the comparison.

In some embodiments, a method for tracking teeth movement correction can be accomplished by creating a virtual teeth model that models a number of physical teeth as virtual teeth, such as on a computing device. A virtual treatment process (e.g., an expected teeth arrangement model) can be created that includes one or more treatments having a number of orientations of the number of virtual teeth. In many such embodiments, each treatment is provided by a different appliance.

In various embodiments, a number of virtual markers can be oriented on one or more of the number of virtual teeth in the virtual teeth model. In some such embodiments, a corresponding number of physical markers can be attached on the physical teeth corresponding to the positions of the virtual markers on the virtual teeth.

In this way, the virtual and physical markers can be compared. To accomplish this comparison, in some embodiments, one or more images (e.g., photos, X-rays, etc.) of at least one of the number of physical reference markers can be taken.

In such embodiments, taking multiple images over a period of time to identify a pattern of movement and comparing the positions of the number of physical markers with a corresponding number of virtual markers can be performed. This can be accomplished, for example, by analyzing the multiple images taken and identifying physical teeth positional information therefrom and then comparing the physical teeth positional information against virtual teeth positional information.

In some embodiments, the position of the physical markers on the image can be detected. Such markers can be compared (e.g., matched) with the virtual teeth model to obtain actual teeth positions relative to the virtual teeth model. In this way, a determination can be made whether a particular appliance is suitable for restarting the treatment process. This comparison can also be useful in generally identifying where in the treatment process a patient is.

This can be useful in comparing the movement of teeth. For example, in some embodiments, periodic subsequent images can be taken to obtain a sequence of physical teeth positions. Positional information can be used with computer-implemented computational geometry calculations to verify that a physical teeth movement gained in a previous periodic image follows the virtual treatment process.

This information can also be used to see whether a previously fabricated appliance would be a useful starting point for restarting the treatment process. For instance, if the virtual model includes the virtual configurations of the teeth for each appliance, the information can be compared with each particular appliance until a suitable appliance, if any, is identified that can be used to restart the treatment process.

In some embodiments, the positional information about an actual appliance may have to be provided to the computing device doing the calculations and comparisons. In such instances, the information can be entered by an individual into the computing device, provided in a file readable by the computing device, or can be obtained through analysis of one or more images of the appliance, similar to the methodology used above with respect to obtaining positional information about the current teeth locations.

For example, some embodiments can be designed to use computer-implemented computational geometry calculations to detect the position of the physical markers on an appliance or one or more teeth on an image. In some embodiments, the positional information can be obtained from the shape of the appliance or the shape of a particular tooth or teeth.

In some applications, an advantage of using markers may be that the amount of computing device processing power is less when calculating the location of a number of markers rather than portions of or the entire tooth, teeth, and/or appliance. In such embodiments, the ability to use less processing power may allow a patient or orthodontics office to use a computing device, such as a desktop computing device or local server, to do such calculations. Such ability may result in faster analysis and/or change of treatment.

In another example embodiment, a method can include using a set of positioning appliances shaped to move teeth through a number of successive stages of arrangements of an expected teeth arrangement model where each stage corresponds to a particular positioning appliance. A corresponding number of physical markers can be attached on a number of physical teeth as discussed herein, where the positions of the physical markers on the physical teeth correspond to the positions of the virtual markers on the virtual teeth. Since the positions of the physical markers and virtual markers correspond, the amounts of processing power used for analysis may be less than when non-corresponding positions are used.

One or more current teeth positions can be mapped based upon positions of the number of physical markers attached to the number of physical teeth. The positions of the number of physical markers can be compared with a corresponding number of virtual markers positioned on a number of virtual teeth of a stage in the expected teeth arrangement model. With such comparison information, the determination of whether or not midcourse correction is needed can be made. And, if it is determined that midcourse correction is needed, then a determination of which particular positioning appliance would be most suitable for restarting a treatment process can be made based upon the comparison.

In various embodiments, a computer readable medium can have instructions for causing a device to perform a method. In such embodiments, a computer readable medium can be any medium that can store computer readable information thereon. Suitable examples include optically or magnetically readable forms of media, among others.

Figure 3:
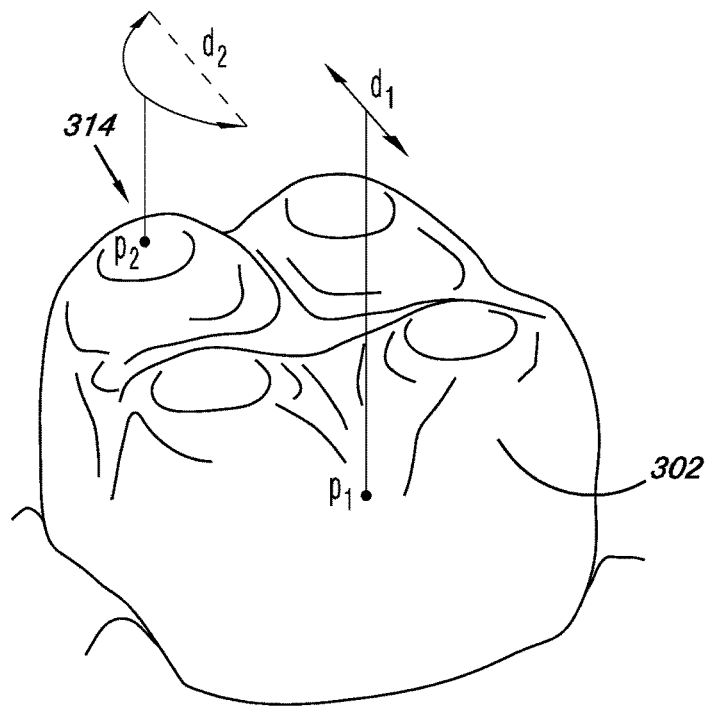
FIG. 3 illustrates a single tooth from FIG. 2 and defines how tooth movement distances can be determined.

Referring now to FIG. 3, the magnitude of any tooth movement achieved by the methods and systems of the present disclosure can be defined in terms of the linear translation of a point P 314 on a tooth 302. Each point $P_i$ will undergo a cumulative translation as that tooth is moved in any of the orthogonal or rotational directions defined in FIG. 2.

That is, while the point will usually follow a non-linear path, there will be a linear distance between any point in the tooth when determined at any two times during the treatment. Thus, an arbitrary point $P_1$ may in fact undergo a true side-to-side translation as indicated by arrow $d_1$, while a second arbitrary point $P_2$ may travel along an arcuate path, resulting in a final translation $d_2$.

In various embodiments, the positions of virtual teeth and physical teeth can be located and/or tracked based upon such positional information, among other types of information. In some embodiments, the points P in FIG. 3 can represent separate physical or virtual markers provided as point objects, points within one or more line objects, and/or points within one or more shape or symbol objects.

As stated herein, the markers can be temporary or permanent in various embodiments. For instance, in some embodiments, the physical markers can be removed. This can be advantageous in some situations. For example, the markers can be removed between the taking of the periodic images.

In this manner, the patient does not have to have the markers on their teeth except for short periods, such as when the images are being taken. For such embodiments, any suitable type of removable affixation mechanism can be used to place and remove the markers (e.g., removable adhesives, removable marker materials, marker materials that dissolve or change color, etc.)

With regard to the types of items that can be used as markers, in various embodiments, the marker can be an attachment or piece of dental work (e.g., filling crown, etc.) that has been applied to a tooth for other orthodontic purpose as, for example, discussed above. In some embodiments, markers are applied that do not serve another purpose may be provided. The markers, for example, can be dental materials, such as dental fillers or adhesives that are being used as markers and not for their typical purpose. In some embodiments, one or more markers can be applied by a type of writing instrument (e.g., a pen or pencil).

In some embodiments, a medically safe material can be used. This can be advantageous in some instances, such as when a marker is to be left in the patient for an extended period.

In various embodiments, markers can include a colorant that is temporarily or permanently visible to the unaided human eye. For example, in some embodiments, one or more physical markers can be provided in the form of a colorant that changes color when the colorant interacts with a catalyst. Such concepts are discussed in more detail below.

Markers can be of any suitable shape. For example, one or more lines (e.g., a line object) can be used which can indicate movement when tracked over time. Symbols and/or shapes (e.g., a shape object), such as a square, triangle, or other shape or symbol can be used for similar purposes.

Further, one or more dots (i.e., point objects) can be used. For example, the use of more than one point can allow for more accurate positioning than a single point, in some instances. The embodiment in FIG. 3, for instance, illustrates a number of points that can be used as markers. In some embodiments, the use of three or more point objects can be used which can allow for easier triangulation of a position of one or more teeth.

Some markers can be placed in positions or sized such that they are invisible or nearly invisible to the unaided human eye unless the teeth are closely examined. For example, a number of small dots may be nearly invisible except upon close examination.

In some embodiments, the marker material may be visible outside the visible range of the human eye. For instance, the material can be radiopaque such that it is viewable in the X-ray spectral range. Thus, in such embodiments, the material may be invisible to the unaided human eye, but visible in the X-ray spectral range.

Some materials may be visible when exposed to a catalyst. For example, materials that change their visible nature when exposed to chemicals, temperature, or different types of light (e.g., ultraviolet, infrared, polarized, etc.) are such materials. Such embodiments can be advantageous since the markers can be viewable for purposes of imaging, but may be less visible or not visible prior to and/or after imaging.

Figure 4:
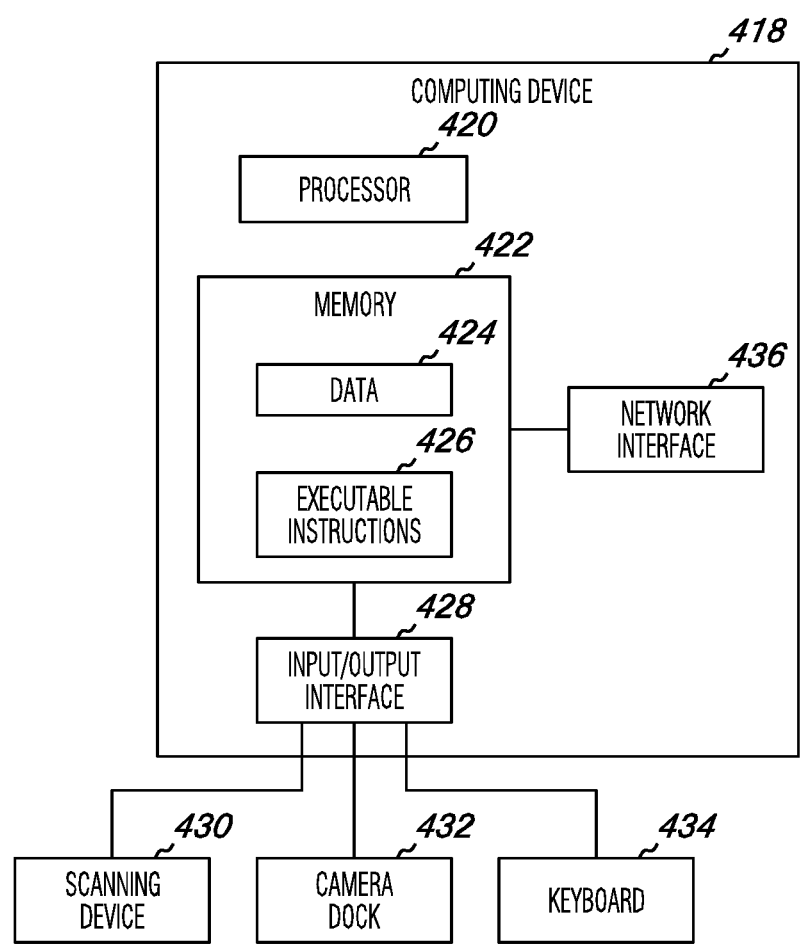
FIG. 4 provides a system for analyzing the positions of various physical teeth and in creating virtual models thereof that can be used with embodiments of the present disclosure.

FIG. 4 provides a system for analyzing the positions of various physical teeth and in creating virtual models thereof that can be used with embodiments of the present disclosure. In the system illustrated in FIG. 4, the system includes a computing device 418 having a processor 420 and memory 422. The memory can include various types of information including data 424 and executable instructions 426 as discussed herein.

Additionally, as illustrated in the embodiment of FIG. 4, a system can include a network interface 436. Such an interface can allow for processing on another networked computing device or such devices can be used to obtain information about the patient or executable instructions for use with various embodiments provided herein.

As illustrated in the embodiment of FIG. 4, a system can include one or more input and/or output interfaces 428. Such interfaces can be used to connect the computing device with one or more input or output devices. For example, in the embodiment illustrated in FIG. 4, the system includes connectivity to a scanning device 430, a camera dock 432, and a keyboard.

Such connectivity allows for the input of image information (e.g., scanned images or digital pictures, etc.) or instructions (e.g., input via keyboard) among other type of information. Although some embodiments may be distributed among various computing devices within one or more networks, such systems as illustrated in FIG. 4 can be beneficial in allowing for the capture, calculation, and analysis of the various information discussed herein.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A non-transitory computer readable medium, having instructions, which when executed by a processor, cause a device to:
   create a virtual teeth model corresponding to a number of physical teeth of a particular patient;
   create a virtual expected teeth arrangement model from the virtual teeth model including a number of successive stages of arrangements of the virtual teeth model;
   receive one or more images taken of the number of physical teeth at a particular point in time that corresponds to one of the number of successive stages;
   compare the position of at least one of the number of physical teeth with a position of the corresponding at least one of the number of virtual teeth at the particular stage to determine a difference between the position of the at least one of the number of physical teeth with a position of the corresponding at least one of the number of virtual teeth; and
   determine whether midcourse correction is needed.

2. The medium of claim 1, where the instructions cause the device to determine which particular positioning appliance of a set of positioning appliances would be most suitable for restarting a treatment process based upon the comparison, if it is determined that midcourse correction is needed.

3. The medium of claim 1, where the instructions cause the device to map current teeth position based upon positions of the number of physical teeth determined from the one or more received images.

4. The medium of claim 3, where the instructions to determine whether midcourse correction is needed is based on the determination of the difference between the position of the at least one of the number of physical teeth and the position of the corresponding at least one of the number of virtual teeth.

5. The medium of claim 3, where the instructions to compare the position of at least one of the number of physical teeth with a position of the corresponding at least one of the number of virtual teeth at the particular stage to determine a difference between the position of the at least one of the number of physical teeth with a position of the corresponding at least one of the number of virtual teeth include instructions to analyze multiple images taken and identify teeth positional information therefrom, where the positional information is compared against virtual teeth positional information.

6. The medium of claim 1, where the instructions cause the device to identify a pattern of movement and compare the position of at least one of the number of physical teeth with a position of the corresponding at least one of the number of virtual teeth at the particular stage to determine a difference between the position of the at least one of the number of physical teeth with a position of the corresponding at least one of the number of virtual teeth by analyzing multiple images taken and identifying physical teeth positional information therefrom, where the physical teeth positional information is compared against virtual teeth positional information.

7. A system for tracking teeth movement, comprising:
a processor; and
a memory coupled to the processor, wherein the memory includes instructions to:
create a virtual teeth model corresponding to a number of physical teeth of a particular patient;
create a virtual expected teeth arrangement model from the virtual teeth model including a number of successive stages of arrangements of the virtual teeth model;
receive one or more images taken of the number of physical teeth at a particular point in time that corresponds to one of the number of successive stages;
compare the position of at least one of the number of physical teeth with a position of the corresponding at least one of the number of virtual teeth at the particular stage to determine a difference between the position of the at least one of the number of physical teeth with a position of the corresponding at least one of the number of virtual teeth; and
determine whether midcourse correction is needed.

8. The system of claim 7, where the instructions cause the device to determine which particular positioning appliance of a set of positioning appliances would be most suitable for restarting a treatment process based upon the comparison, if it is determined that midcourse correction is needed.

9. The system of claim 7, where the instructions cause the device to map current teeth position based upon positions of the number of physical markers attached to the at least one of the number of physical teeth.

10. The system of claim 9, where the instructions to compare the position of the at least one of the number of physical markers with a position of the corresponding at least one of the number of virtual markers include instructions to analyze the image taken and identifying teeth positional information therefrom.

11. The system of claim 9, where the instructions to compare include comparing a position of the at least one of the number of physical markers with a position of a corresponding at least one of the number of virtual markers.

12. The system of claim 11, where the instructions comparing a position of the at least one of the number of physical markers with a position of a corresponding at least one of the number of virtual markers include instructions to analyze multiple images taken and identifying teeth positional information therefrom, where the positional information is compared against virtual teeth positional information.

13. The system of claim 11, where receiving one or more images includes receiving multiple images and comparing those images to identify a pattern of movement.

14. The system of claim 13, analyzing the multiple images taken and identifying physical teeth positional information therefrom.

15. The system of claim 7, where receiving one or more images includes receiving multiple images over a period of time and comparing those images to identify a pattern of movement.

16. The system of claim 7, where the received one or more image comprises at least one photo.

17. The system of claim 7, where the received one or more image comprises at least one X-ray image.

18. The system of claim 7, where the received one or more image comprises at least one three dimensional image.

19. The system of claim 7, where receiving one or more images includes receiving multiple images over a period of time and comparing those images and teeth positions in at least one of the number of successive stages of arrangements of the virtual tooth model to identify a pattern of movement.

* * * * *